United States Patent [19]

Lassman et al.

[11] 4,082,850
[45] Apr. 4, 1978

[54] METHOD OF TREATING DERMAL INFLAMMATIONS

[75] Inventors: Howard B. Lassman, Flemington; William J. Novick, Jr., Lebanon, both of N.J.

[73] Assignee: American Hoechst Corporation, Bridgewater, N.J.

[21] Appl. No.: 677,544

[22] Filed: Apr. 16, 1976

[51] Int. Cl.² .......................................... A61K 31/335
[52] U.S. Cl. ................................................... 424/278
[58] Field of Search ....................... 424/278; 260/333

[56] References Cited

FOREIGN PATENT DOCUMENTS 818,055  7/1974  Belgium.

*Primary Examiner*—Stanley J. Friedman
*Attorney, Agent, or Firm*—Curtis, Morris & Safford

[57] ABSTRACT

A method of treating dermal inflammation by topically administering to a patient an effective amount of a 6,11-dihydrodibenz[b,e]oxepinalkanoic acid, physiologically tolerable salt thereof, derivative thereof, or diacid precursor thereof is described.

23 Claims, 1 Drawing Figure

U.S. Patent    April 4, 1978    4,082,850
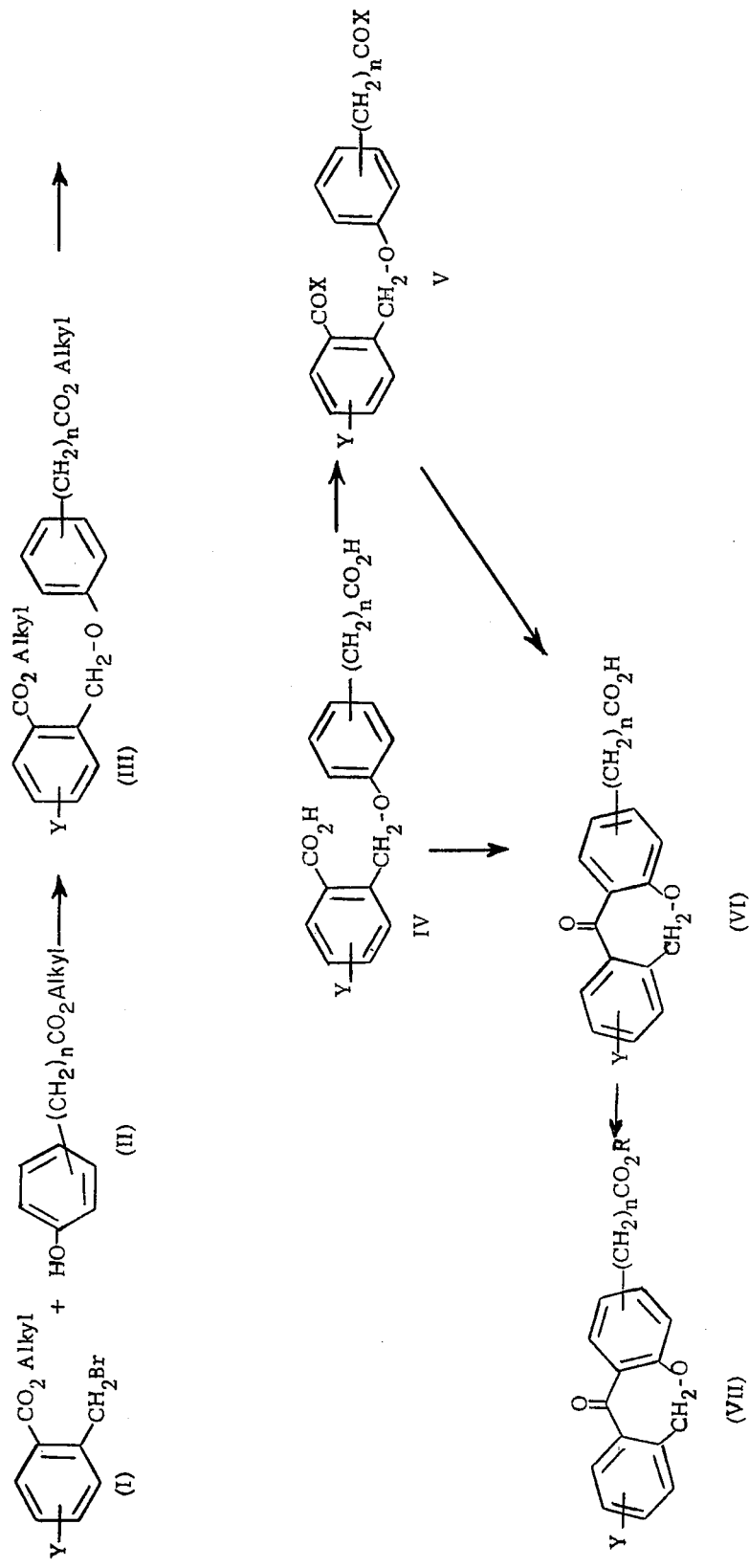

METHOD OF TREATING DERMAL INFLAMMATIONS

This invention relates to a novel method of treating inflammations in the dermal layers of mammals which involves the administering to a patient an effective amount of a 6,11-dihydro[b,e]oxepin-alkanoic acid, physiologically tolerable salt thereof, derivative thereof or diacid percursor thereof, and to compositions containing an aforesaid compound.

Most of the compounds disclosed herein for the treatment of dermal inflammations have previously been described and demonstrated to be systemic antiinflammatory agents by Helsley et al. in U.S. patent application Ser. No. 459,774, filed Apr. 10, 1974 which is a continuation in part of application Ser. No. 394,801, filed Sept. 6, 1973, now abandoned, Ueno et al. in Belgian Pat. No. 818,055 published Nov. 18, 1974 and McFadden et al. U.S. Pat. application Ser. No. 600,210, filed July 30, 1975. However, the aforesaid compounds have not, heretofore, been described as topical antiinflammatory agents enabling their use in the treatment of dermal inflammations. Utility of these compounds as described herein as surprising and unanticipated for several reasons. The skin is a unique organ; while the etiology of inflammations of the skin is not completely understood, it is generally recognized, however, that it differs substantially from the etiology of systemic inflammations. Further, absorption of compounds through the multifold dermal layers involves quite a different set of physiochemical requirements than absorption/distribution processes on a systemic basis. For these reasons it is appreciated that it is not expected that systemically effective antiinflammatory agents are also topically effective, especially in the case of nonsteroids. Further surprising is the efficacy of the topical antiinflammatory agents described herein. Their efficacy is either comparable or superior to steriods which are well recognized potent antiinflammatory agents. Additionally, it is surprising that the topical antiinflammatory agents of the present invention while exhibiting comparable or superior efficacy to the steroids do not exhibit the serious side effects which often accompany topical steroid therapy.

It is also very surprising that the diacid percursors of 6,11-dihydrodibenz[b,e]oxepin-alkanoic acid demonstrate rather potent activity as topical antiinflammatory agents while being inactive or insignificantly active as systemic antiinflammatory agents. The same supplies to 3-(6,11-dihydro-11-oxo-dibenz[b,e]oxepin-2-yl)propionic acid. This further illustrates the fact that topical antiinflammatory activity cannot be predicated upon a showing of systemic antiinflammatory activity.

The method of the invention involves utilization of a compound of the formulae:

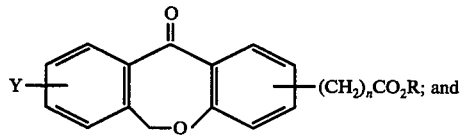

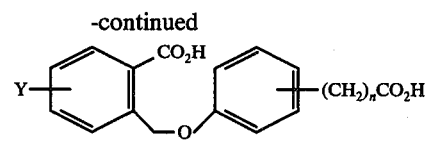

in which Y is hydrogen, alkyl of from 1 to 4 carbon atoms, alkoxy of from 1 to 4 carbon atoms, halogen or trifluoromethyl; R is hydrogen or straight or branched chain alkyl of from 1 to 6 carbon atoms; and $n$ is an integer from 1 to 7.

The compounds used in the method of this invention are prepared by a multi-step sequence of reactions as described below and illustrated in the attached flow sheet, in which Y and $n$ are as defined earlier, R is alkyl and X is halogen.

A lower alkyl ester (I), i.e., an ester with 1 to 4 carbon atoms in the alcoholic unit, of a substituted α-bromotoluic acid is allowed to react with a lower alkyl ester of a hydroxyphenylalkanoic acid (II) in a solvent such as acetone, butanone, ethanol, or dimethylformamide with a base such as potassium carbonate or sodium hydride at a temperature of 0° C to 120° C for a time of 5 minutes to 12 hours to provide a diester of a substituted carboxybenzyloxyphenylalkanoic acid (III), which is then saponified with a base such as sodium or potassium hydroxide in a solvent such as ethanol or water for a time of from 15 minutes to 24 hours at a temperature of 25° C to 125° C to provide a dicarboxylic acid (IV), a topical antiinflammatory of the invention.

The dicarboxylic acid (IV) is cyclized by treatment with a dehydrating medium such as polyphosphoric acid, ethanolphosphorous pentoxide, or sulfuric acid with or without a solvent such as tetramethylenesulfone or acetic acid at a temperature of 50° to 125° C for from 15 minutes to 12 hours to provide a 6,11-dihydro-11-oxodibenz[b,e]oxepin-alkanoic acid (VI), a topical antiinflammatory of the invention.

Alternatively the dicarboxylic acid is converted to a diacid halide (V) by treatment with a sufficient amount of an agent, such as thionyl halide or phosphorous pentahalide. The diacid halide is reacted under Friedel-Crafts conditions and then hydrolyzed by a method known to the art to provide a 6,11-dihydrodibenz[b,e]oxepin-alkanoic acid (VI).

A 6,11-dihydrodibenz[b,e]oxepin-alkanoic acid is allowed to react with an alcohol of the formula R—OH in the presence of an acid, such as sulfuric, hydrochloric or p-toluene sulfonic acid, at a temperature of 50° to 90° C for from 15 minutes to 15 hours to provide a 6,11-dihydrodibenz[b,e]oxepinalkanoic acid ester (VII), a topical antiinflammatory of the invention.

Physiologically tolerable salts of this invention are those prepared from various organic bases such as ethanolamine, diethanolamine and dimethylethanolamine.

In use, a composition containing an effective amount of the active compound is administered topically to the inflamed area of a patient having a dermal inflammation.

The compounds described herein are suitable as topical antiinflammatory agents due to their ability to suppress dermal inflammations in mammals. One method of assessing this ability is the croton oil induced edema assay in mice [Endocrinology, 77, 625 (1965); Clin. Pharmacol. and Therap., 16, 900 (1974)]. Accordingly, representative compounds were applied to the ear of a mouse in which said edema was induced. It was found, as shown below in Table 1, that these compounds are very effective in reducing this edema. In this table the results are shown in terms of a percent decrease of edema at a mg. dose/ear.

TABLE I

| Compound | % decrease of edema | dose mg/ear |
|---|---|---|
| 4-(2-carboxybenzyloxy)-phenylacetic acid | 39 | 2.5 |
| 4-(2-carboxy-5-chloro-benzyloxy)phenyl acetic acid | 73 | 2.5 |
| 4-(2-carboxy-5-methoxy-benzyloxy)phenyl acetic acid | 53 | 2.5 |
| 4-(2-carboxy-6-chlorobenzyl-oxy)phenyl acetic acid | 33 | 2.5 |
| 4-(2-carboxybenzyloxy)-phenylpropionic acid | 70 | 2.5 |
| 4-[4-(2-carboxybenzyloxy)phenyl]butyric acid | 66 | 2.5 |
| 6-[4-(2-carboxybenzyloxy)phenyl]caproic acid | 77 | 2.5 |
| 6,11-dihydro-11-oxodibenz-[b,e]oxepin-2-acetic acid | 50 | 4.4 |
| 6,11-dihydro-8-chloro-11-oxo-dibenz[b,e]oxepin-2-acetic acid | 76 | 2.5 |
| 6,11-dihydro-8-methoxy-11-oxodibenz[b,e]oxepin-2-acetic acid. | 15 | 2.5 |
| 6,11-dihydro-7-chloro-11-oxodibenz[b,e]oxepin-2-acetic acid | 60 | 2.5 |
| 6,11-dihydro-9-trifluoro-methyl-11-oxodibenz[b,e]-2-acetic acid | 71 | 2.5 |
| n-butyl 6,11-dihydro-11-oxo-dibenz[b,e]oxepin-2-acetate | 24 | 2.5 |
| n-amyl 6,11-dihydro-11-oxo-dibenz[b,e]oxepin-2-acetate | 21 | 2.5 |
| 4-(6,11-dihydro-11-oxodibenz-[b,e]oxepin-2-yl)butyric acid | 68 | 2.5 |
| 3-(6,11-dihydro-11-oxodibenz-[b,e]oxepin-2-yl)propionic acid | 73 | 2.5 |
| methyl 4-(6,11-dihydro-11-oxodibenz[b,e]oxepin-2-yl)-butyrate | 41 | 2.5 |
| 8-(6,11-dihydro-11-oxodibenz-[b,e]oxepin-2-caprylic acid | 50 | 1.5 |
| 6-(6,11-dihydro-11-oxodibenz-[b,e]oxepin-2-yl)caproic acid | 66 | 2.5 |
| isopropyl 4-(6,11-dihydro-11-oxodibenz[b,e]oxepin-2-yl)-butyrate | 59 | 2.5 |

Additionally, other assays can be used to assess the suitability of the compounds described herein to treat dermal inflammations, such as the oxazolone sensitization test [Br. Journal of Pharmacol., 43, 403–408 (1971)].

To effectively utilize the topical antiinflammatory agents of this invention, said agents may be incorporated into a solution, suspension, ointment, cream or salve. These preparations should contain at least 0.01% of the active compound but may be varied to be between 0.05 and about 20% of the weight thereof. The amount of active compound in such compositions is such that a suitable dosage will be obtained. Preferred compositions for the treatment of dermal inflammations are those containing between 0.1 and 10% of the active compound.

The topical compositions may also include the following components: water, fixed oils, polyethylene glycols, glycerol, petroleum, stearic acid, beeswax, other synthetic solvents or mixtures thereof; antibacterial agents such as benzyl alcohol or methyl paraben; antioxidants such as α-tocopherol acetate; chelating agents such as ethylenediaminetetracetic acid; buffers such as acetates, citrates or phosphates; emulsifying agents such as polyoxyethylene monooleate and coloring materials and adjuvants such as ferric oxide or talc.

The topical preparations can be enclosed in tubes, bottles or jars made of metal, glass or plastic.

Illustrative of the preparation of the antiinflammatory agents of the invention are given below in the following examples.

EXAMPLE I a. A mixture of 100 g of ethyl o-toluate, 100 g of N-bromosuccinimide and 0.3 g of benzoyl peroxide in 1 liter of carbon tetrachloride is heated under reflux for 3 hours with stirring and filtered. The filtrate is washed with 3% aqueous sodium hydroxide and then with water, dried over magnesium sulfate and concentrated under reduced pressure to provide ethyl α-bromo-o-toluate as an oil.

b. A mixture of 20 g of ethyl α-bromo-o-toluate, 14.4 g of ethyl 4-hydroxyphenylacetate, b 44 g of potassium carbonate, 1.3 g of potassium iodide and 200 ml of 2-butanone is refluxed for sixteen hours. The salts are filtered and washed with ether and concentrated in vacuo to an oil. The oil is dissolved in ether and washed with sodium bicarbonate followed by water, dried over magnesium sulfate and evaporated to ethyl 4-(2-ethoxycarbonylbenzyloxy)phenylacetate as an oil.

c. A mixture of 100 g of ethyl 4-(2-ethoxycarbonylbenzyloxy)phenylacetate, 100 g of potassium hydroxide, and 1 liter of ethanol is refluxed with stirring for 3 hours. The mixture is concentrated in vacuo and the residue is dissolved in water. The solution is extracted with ether and the aqueous layer is acidified with hydrochloric acid. The precipitate is filtered and washed with hot ether to provide colorless crystals, mp 176°–178° C, of 4-(2-carboxybenzyloxy)phenylacetic acid.

Analysis: Calculated for $C_{16}H_{14}O_5$: 67.13%C; 4.89%H. Found: 67.48%C; 4.88%H.

EXAMPLE 2

A. To 49 ml of absolute ethanol is added with vigorous stirring, 81 g of phosphorus pentoxide. After addition, the mixture is allowed to stir at 95°–100° C for 1 hour, 400 ml of tetramethylene sufone are added and the temperature is adjusted to 86°–90° C. Then, 38.5 g of 4-(2-carboxybenzyloxy)phenylacetic acid, Example 1, are added, the mixture is stirred for 4 hours and poured onto ice water. The aqueous mixture is made basic with sodium hydroxide and extracted with toluene. Cooling of the aqueous layer followed by acidification with concentrated hydrochloric acid gives light brown crystals. Recrystallization from acetic acid-water or from dimethoxyethane provides colorless crystals, mp 126°–128° C of 6,11-dihydro-11-oxodibenz[b,e]oxepin-2-acetic acid.

Analysis: Calculated for $C_{16}H_{12}O_4$: 71.64%C; 4.51%H. Found: 71.44%C; 4.58%H.

Treatment of this acid with ethanolic potassium hydroxide provides the potassium salt, mp 214°–216° C.

Analysis: Calculated for $C_{16}H_{11}KO_4$: 62.73%C; 3.62%H. Found: 62.04%C; 3.45%H.

b. As an alternative to step a above, 43.7 g of polyphosphoric acid are added to 10.0 g of 4-(2-carboxybenzyloxy)phenylacetic acid in 35 ml of glacial acetic acid. The mixture is vigorously stirred at 76° C for 1⅔ hours and then hydrolyzed with 250 ml of water, the temperature being kept at 40° C. The precipitate which separates is collected and, when recrystallized from 2-propanol-water, provides pale yellow crystals, mp 137°–138° C, of 6,11-dihydro-11-oxodibenz[b,e]oxepin-2-acetic acid.

Analysis: Calculated for $C_{16}H_{12}O_4$: 71.64%C, 4.51%H. Found: 71.58%C; 4.58%H.

EXAMPLE 3

A mixture of 42 g of 6,11-dihydro-11-oxodibenz[b,e]oxepin-2-acetic acid. Example 2, 750 ml of methanol and 17 ml of concentrated sulfuric acid is refluxed for 24 hours. The reaction mixture is diluted with water and extracted with benzene. After drying over magnesium sulfate, the benzene is concentrated to an oil. The precipitate resulting from addition of hexane is recrystallized from benzene-methanol to provide colorless crystals, mp 74°–76° C, of methyl 6,11-dihydro-11-oxodibenz[b,e]oxepin-2-acetate.

Analysis: Calculated for $C_{17}H_{14}O_4$: 72.33%C; 5.00%H. Found: 72.47%C; 5.11%H.

EXAMPLE 4

Reaction of 6,11-dihydro-11-oxodibenz[b,e]oxepin-2-acetic acid, Example 2, with 2-propanol as described in Example 3 provides isopropyl 6,11-dihydro-11-oxodibenz[b,e]oxepin-2-acetate as colorless crystals, mp 67°–68.5° C.

Analysis: Calculated for $C_{19}H_{18}O_4$: 73.53%C; 5.85%H. Found: 73.59%C; 5.92%H.

EXAMPLE 5

A mixture of 7.0 g of 6,11-dihydro-11-oxodibenz[b,e]oxepin-2-acetic acid, Example 2, 175 ml of n-propanol, and 4.6 ml of concentrated sulfuric acid is refluxed for 17 hours. The reaction mixture is permitted to cool and the solvent removed leaving an oil. The oil is dissolved in ether and washed successively with water, a 5% sodium hydroxide solution and water and dried and the ether removed to give a yellow oil which crystallizes upon standing. The solid is dried on a porous plate resulting in an off-white solid, mp 30°–32° C, of n-propyl 6,11-dihydro-11-oxodibenz[b,e]oxepin-2-acetate.

Analysis: Calculated for $C_{19}H_{18}O_4$: 73.53%C; 5.85%H. Found: 73.33%C; 5.95%H.

EXAMPLE 6

Reaction of 6,11-dihydro-11-oxodibenz[b,e]oxepin-2-acetic acid, Example 2, with n-butanol as described in Example 5 provides n-butyl 6,11-dihydro-11-oxodibenz[b,e]oxepin-2-acetate.

Analysis: Calculated for $C_{20}H_{20}O_4$: 74.05%C; 6.21%H. Found: 74.08%C; 6.17%H.

EXAMPLE 7

A mixture of 4.35 g of 6,11-dihydro-11-oxodibenz[b,e]oxepin2-acetate, Example 2, 108 ml of n-amyl alcohol and 3 ml of concentrated sulfuric acid is refluxed for 20 hours. The reaction mixture is permitted to cool and the solvent removed leaving an oil. The oil is dissolved in ether and washed successively with water, a saturated sodium bicarbonate solution and water and dried. The ether is removed leaving a brown oil which is chromatographed on a silica gel dry column to give a light yellow oil of n-amyl 6,11-dihydro-11-oxodibenz[b,e]oxepin-2-acetate.

Analysis: Calculated for $C_{21}H_{22}O_4$: 74.53%C; 6.55%H. Found: 74.15%C; 6.74%H.

EXAMPLE 8 a. Reaction of ethyl 4-fluoro-o-toluate with N-bromosuccinimide as described in Example 1a provides ethyl α-bromo-4-fluoro-o-toluate.

b. Reaction of ethyl α-bromo-4-fluoro-o-toluate with ethyl p-hydroxyphenylacetate as described in Example 1b provides ethyl 4-(2-ethoxycarbonyl-5-fluorobenzyloxy)phenylacetate.

c. Reaction of ethyl 4-(2-ethoxycarbonyl-5-fluorobenzyloxy)phenylacetate with potassium hydroxide as described in Example 1c provides 4-(2-carboxy-5-fluorobenzyloxy)phenylacetic acid.

EXAMPLE 9

Reaction of 4-(2-carboxy-5-fluorobenzyloxy)phenylacetic acid, Example 8, with the phosphorus pentoxide-ethanol complex as previously described in Example 2 provides 6,11-dihydro-8-fluoro-11-oxodibenz[b,e]oxepin-2-acetic acid.

EXAMPLE 10 a. Reaction of ethyl 4-chloro-o-toluate with N-bromosuccinimide as described in Example 1a provides ethyl α-bromo-4-chloro-o-toluate as an oil.

b. Reaction of ethyl α-bromo-4-chloro-o-toluate with ethyl p-hydroxyphenylacetate as described in Example 1b provides ethyl 4-(2-ethoxycarbonyl-5-chlorobenzyloxy)phenylacetate as a yellow oil.

c. Reaction of ethyl 4-(2-ethoxycarbonyl-5-chlorobenzyloxy)phenylacetate with potassium hydroxide as described in Example 1c provides 4-(2-carboxy-5-chlorobenzyloxy)phenylacetic acid as a colorless solid, mp 197°–201° C.

Analysis: Calculated for $C_{16}H_{13}ClO_5$: 59.92%C; 4.08%H. Found: 59.73%C; 4.09%H.

EXAMPLE 11

Reaction of 4-(2-carboxy-5-chlorobenzyloxy)phenylacetic acid with the phosphorus pentoxide-ethanol complex as described in Example 2 at a temperature of 85°–90° C provides 6,11-dihydro-8-chloro-11-oxodibenz-[b,e]oxepin-2-acetic acid as colorless crystals, mp 188°–190° C.

Analysis:

Calculated for $C_{16}H_{11}ClO_4$: 63.48%C; 3.66%H.
Found: 63.28%C; 3.67%H.

EXAMPLE 12 a. Reaction of ethyl 5-chloro-o-toluate with N-bromosuccinimide as described in Example 1a provides ethyl α-bromo-5-chloro-o-toluate.

b. Reaction of ethyl α-bromo-5-chloro-o-toluate with ethyl p-hydroxyphenylacetate as described in Example 1b provides ethyl 4-(2-ethoxy-carbonyl-4-chlorobenzyloxy)phenylacetate.

c. Reaction of ethyl 4-(2-ethoxycarbonyl-4-chlorobenzyloxy)phenylacetate with potassium hydroxide as described in Example 1c provides 4-(2-carboxy-4-chlorobenzyloxy)phenylacetic acid, mp 205°–208° C.

Analysis:

Calculated for $C_{16}H_{13}ClO_5$: 59.92%C; 4.08%H.
Found: 60.06%C; 4.14%H.

EXAMPLE 13

Reaction of 4-(2-carboxy-4-chlorobenzyloxy)phenylacetic acid, Example 14, with the phosphorus pentoxide-ethanol complex as described in Example 2 provides 6,11-dihydro-9-chloro-11-oxodibenz[b,e]oxepin-2-acetic acid, mp 169°–171° C.

Analysis:
Calculated for $C_{16}H_{11}ClO_4$: 63.48%C; 3.66%H; 11.71%Cl.
Found: 63.20%C; 3.79%H; 11.51%Cl.

EXAMPLE 14 a. Reaction of ethyl 5-trifluoromethyl-o-toluate with N-bromosuccinimide as described in Example 1a provides ethyl α-bromo-5-trifluoromethyl-o-toluate.

b. Reaction of ethyl α-bromo-5-trifluoromethyl-o-toluate with ethyl p-hydroxyphenylacetate as described in Example 1b provides ethyl 4-(2-ethoxycarbonyl-4-trifluoromethylbenzyloxy)phenylacetate.

c. Reaction of ethyl 4-(2-ethoxycarbonyl-4-trifluoromethylbenzyloxy)phenylacetate with potassium hydroxide as described in Example 1c provides 4-(2-carboxy-4-trifluoromethylbenzyloxy)phenylacetic acid, mp 185°–187° C.

Analysis:
Calculated for $C_{17}H_{13}F_3O_5$: 57.63%C; 3.70%H.
Found: 57.31%C; 3.73%H.

EXAMPLE 15

Reaction of 4-(2-carboxy-4-trifluoromethylbenzyloxy)phenylacetic acid, Example 16, with the phosphorus pentoxide-ethanol complex as described in Example 1d provides 6,11-dihydro-9-trifluoromethyl-11-oxodibenz[b,e]oxepin-2-acetic acid, mp 152°–155° C.

Analysis:
Calculated for $C_{17}H_{11}F_3O_4$: 60.72%C; 3.30%H.
Found: 60.68%C; 3.38%H.

EXAMPLE 16 a. Reaction of ethyl 4-methoxy-o-toluate with N-bromosuccinimide as described in Example 1a provides ethyl α-bromo-4-methoxy-o-toluate as a colorless liquid.

b. Reaction of ethyl α-bromo-4-methoxy-o-toluate with ethyl p-hydroxyphenylacetate as described in Example 1b provides ethyl 4-(2-ethoxycarbonyl-5-methoxybenzyloxy)phenylacetate as a yellow oil.

c. Reaction of ethyl 4-(2-ethoxycarbonyl-5-methoxybenzyloxy)phenylacetate with potassium hydroxide as described in Example 1c provides 4-(2-carboxy-5-methoxybenzyloxy)phenylacetic acid as colorless crystals, mp 200°–208° C.

Analysis:
Calculated for $C_{17}H_{16}O_6$: 64.56%C; 5.10%H.
Found: 64.25%C; 5.16%H.

EXAMPLE 17

Reaction of 4-(2-carboxy-5-methoxybenzyloxy)phenylacetic acid, Example 18, with the phosphorus pentoxide-ethanol complex as described in Example 2 at a temperature of 85°–88° C provides 6,11-dihydro-8-methoxy-11-oxodibenz[b,e]oxepin-2-acetic acid as a colorless solid, mp 163°–165° C.

Analysis:
Calculated for $C_{17}H_{14}O_5$: 68.45%C; 4.73%H.
Found: 68.37%C; 4.94%H.

EXAMPLE 18 a. Reaction of ethyl 5-fluoro-o-toluate with N-bromosuccinimide as described in Example 1a provides ethyl α-bromo-5-fluoro-o-toluate as an oil.

b. Reaction of ethyl α-bromo-5-fluoro-o-toluate with ethyl p-hydroxyphenylacetate as described in Example 1b provides ethyl 4-(2-ethoxycarbonyl-4-fluorobenzyloxy)phenylacetate as an oil.

c. Reaction of ethyl 4-(2-ethoxycarbonyl-4-fluorobenzyloxy)phenylacetate with potassium hydroxide as described in Example 1c provides colorless crystals, mp 195°–197° C of 4-(2-carboxy-4-fluorobenzyloxy)phenylacetic acid.

Analysis:
Calculated for $C_{16}H_{13}FO_5$: 63.16%C; 4.31%H.
Found: 63.27%C; 4.34%H.

EXAMPLE 19

Reaction of 4-(2-carboxy-4-fluorobenzyloxy)phenylacetic acid, Example 18, with the phosphorus pentoxide-ethanol complex as previously described in Example 1d provides beige crystals, mp 173°–175° C, of 6,11-dihydro-9-fluoro-11-oxodibenz[b,e]oxepin-2-acetic acid.

Analysis:
Calculated for $C_{16}H_{11}FO_4$: 67.13%C; 3.87%H; 6.64%F.
Found: 67.05%C; 4.04%H; 6.46%F.

EXAMPLE 20 a. Reaction of ethyl 3-chloro-o-toluate with N-bromosuccinimide as described in Example 1a provides ethyl α-bromo-3-chloro-o-toluate as an oil.

b. Reaction of ethyl α-bromo-3-chloro-o-toluate with ethyl p-hydroxyphenylacetate as described in Example 1b provides ethyl 4-(2-chloro-6-ethoxycarbonylbenzyloxy)phenylacetate as an oil.

c. Reaction of ethyl 4-(2-chloro-6-ethoxycarbonylbenzyloxy)phenylacetate with potassium hydroxide as described in Example 1c provides 4-(6-carboxy-2-chlorobenzyloxy)phenylacetic acid as a colorless solid, mp 171°–173° C.

Analysis:
Calculated for $C_{16}H_{13}ClO_5$: 59.62%C; 4.08%H.
Found: 59.85%C; 4.06%H.

EXAMPLE 21

Reaction of 4-(6-carboxy-2-chlorobenzyloxy)phenylacetic acid, Example 20, with the phosphorus pentoxide-ethanol complex as described in Example 2 at a temperature of 86° C provides 6,11-dihydro-7-chloro-11-oxodibenz[b,e]oxepin-2-acetic acid as beige crystals, mp 173°–176° C.

Analysis:
Calculated for $C_{16}H_{11}ClO_4$: 63.48%C; 3.66%H.
Found: 62.93%C; 3.64%H.

EXAMPLE 22

A mixture of 22.0 g of ethyl 3-(4-hydroxyphenyl)propionate, 27.4 g of ethyl α-bromo-o-toluate, 62.4 g of potassium carbonate and 2.0 g of sodium iodide in 450 ml of 2-butanone is refluxed for 17 hours. After the reaction mixture is permitted to cool, filtered and washed with ether and the solvent removed under reduced pressure leaving a dark yellow oil. The oil is dissolved in either and the ethereal solution is washed successively with water and 5% sodium hydroxide, dried and filtered and the ether removed under reduced pressure leaving a yellow oil. The oil is refluxed with 71.8 g of potassium hydroxide, 358 ml of 95% ethanol and 36 ml of water for 17 hours. After the reaction mixture is permitted to cool the solvent is removed under reduced pressure leaving a semi-solid. This product is dissolved in water and the aqueous solution washed with ether. The aqueous solution is acidified to pH 2 with hydrochloric acid which causes a yellow precipitate with is collected by filtration, washed with acetonitrile and dried. The product is recrystallized from an ethanol-water mixture to produce colorless crystals, mp 176°–178° C, of 3-[4-(2-carboxybenzoyloxy)phenyl]propionic acid.

Analysis:
Calculated for $C_{17}H_{16}O_5$: 67.98%C; 5.37%H.
Found: 67.76%C; 5.37%H.

EXAMPLE 23

To 7.4 ml of absolute ethanol under nitrogen is carefully added 10.4 g of phosphorous pentoxide. After total addition the mixture is stirred at 110° C for 1 hour and 53.1 ml of sulfolane is added and the temperature adjusted to 85° C. To this mixture is added 5.0 g of 3-[4-(2-carboxybenzyloxy)phenyl]propionic acid and the reaction is stirred for 3.5 hours while maintaining the temperature at 85° C. The reaction mixture is poured into 1 liter of ice-water, basified with sodium hydroxide pellets, extracted with toluene and the aqueous phase is acidified with hydrochloric acid causing a precipitate to appear. The precipitate is filtered, triturated with isopropyl alcohol and dried giving a tan solid, mp 128°–130° C, of 3-(6,11-dihydro-11-oxodibenz[b,e]oxepin-2-yl)propionic acid.

Analysis:
Calculated for $C_{17}H_{14}O_4$: 72.32%C; 4.99%H.
Found: 72.23%C; 4.97%H.

EXAMPLE 24

The substitution of ethyl 4-(4-hydroxyphenyl)butyrate for ethyl 3-(4-hydroxyphenyl)propionate into the manipulative procedure described in Example 22 produces an oil which solidifies upon standing. The solid is filtered and washed with water and then recrystallized from acetonitrile to provide a light tan solid, mp 149°–150° C, of 4-[4-(2-carboxybenzyloxy)phenyl]butyric acid.

Analysis:
Calculated for $C_{18}H_{18}O_5$: 68.77%C; 5.77%N.
Found: 68.52%C; 5.69%N.

EXAMPLE 25

To a solution under nitrogen of 5.0 g of 4-[4-(2-carboxybenzyloxy)phenyl]butyric acid in 17.5 ml of glacial acetic acid is added 22.5 of polyphosphoric acid and the reaction mixture is stirred at 95° C for 3 hours. 250 ml of water is added causing a precipitate with is collected by filtration. The precipitate is recrystallized from benzene to provide an off-white solid, mp 116°–118° C, of 4-(6,11-dihydro-11-oxodibenz[b,e]oxepin-2-yl)butyric acid.

Analysis:
Calculated for $C_{18}H_{16}O_4$: 72.95%C; 5.44%H.
Found: 72.79%C; 5.44%H.

EXAMPLE 26

A mixture of 2.6 g of 4-(6,11-dihydro-11-oxodibenz[b,e]oxepin-2-yl)butyric acid, Example 25, and 0.8 g of AMBERLITE IR-120H C.P. in 25 ml of methanol is refluxed for 16 hours, cooled, diluted with ether and filtered. The filtrate is washed successively with a 5% aqueous sodium hydroxide solution and washed with water, dried, filtered, and concentrated in vacuo, leaving a solid which is recrystallized from methanol to give off-white crystals, mp 83°–85° C, of methyl 4-(6,11-dihydro-11-oxodibenz[b,e]oxepin-2-yl)butyrate.

Analysis: Calculated for $C_{19}H_{18}O_4$: 73.53%C; 5.85%H. Found: 73.61%C; 5.92%H.

EXAMPLE 27

The substitution of ethyl 8-(4-hydroxyphenyl)caprylate for ethyl 4-(4-hydroxyphenyl)butyrate into the manipulation procedure described in Example 24 provides colorless crystals, m.p. 116°–118° C, of 8-[4-(2-carboxybenzyloxy)phenyl]caprylic acid.

Analysis: Calculated for $C_{22}H_{26}O_5$: 71.32%C; 7.07%H. Found: 71.26%C; 7.14%H.

EXAMPLE 28

3.4 g of polyphosphoric acid are added to a suspension under nitrogen of 1.0 g of 8-[4-(2-carboxybenzyloxy)phenyl]caprylic acid, Example 27, in 2.63 ml of glacial acetic acid. The reaction mixture is stirred at 100° C for 4 hours, it is then diluted with water and allowed to cool and filtered. The filter cake is dissolved in chloroform, the filtrate is extracted with chloroform and the chloroform solutions are combined, washed with water, dried and the chloroform is removed, leaving a solid which is crystallized from acetonitrile to give a solid, m.p. 68°–70° C, of 8-(6,11-dihydro-11-oxodibenz[b,e]oxepin-2-yl)caprylic acid.

Analysis: Calculated for $C_{22}H_{24}O_4$: 74.97%C; 6.86%H. Found: 74.67%C; 7.03%H.

EXAMPLE 29

A mixture of 25.0 g of ethyl 6-(4-hydroxyphenyl)caproate, 32.0 g of ethyl α-bromo-2-toluate, 72.0 g of anhydrous potassium carbonate and 1.0 g of sodium iodide in 600 ml of 2-butanone is refluxed for 16 hours. The mixture is cooled, filtered, washed with ether and the filtrate is concentrated in vacuo, leaving a yellow oil. The oil is dissolved in 100 ml of 95% ethanol and 20 ml of water and 23.5 g of 85% potassium hydroxide are added and the mixture is refluxed for 14 hours. The solution is concentrated in vacuo, leaving a semi-solid which is dissolved in water. The aqueous solution is washed with ether and acidified with ice-cold concentrated hydrochloric acid to provide a white solid which is collected and recrystallized from acetonitrile to provide white crystals, m.p. 138°–140° C, of 6-[4-(2-carboxybenzyloxy)phenyl]caproic acid.

Analysis: Calculated for $C_{20}H_{22}O_5$: 70.16%C; 6.48%H. Found: 70.22%C; 6.57%H.

EXAMPLE 30

8.8 g of phosphorus pentachloride are added to an ice-bath cooled solution of 7.0 g of 6-[4-(2-carboxybenzyloxy)phenyl]caproic acid, Example 29, in 80 ml of benzene. After all the phosphorus pentachloride dissolves, the ice-bath is removed and the resulting yellowish solution is stirred for 4 hours and the benzene is removed in vacuo at 80° C, leaving an amber oil. The oil is dissolved in 80 ml of methylene chloride, the solution is cooled and 10.9 g of stannic chloride are added, resulting in a dark solution which is stirred for 72 hours at ambient temperature, hydrolyzed with 80 ml of 1N hydrochloric acid and stirred for an additional 36 hours. The mixture is separated and the organic phase is concentrated, leaving a gum which is triturated which chloroform, dried and concentrated to give a solid. The solid is recrystallized from acetonitrile to give an off-white product, m.p. 98°-100° C, of 6-(6,11-dihydro-11-oxodibenz[b,e]oxepin-2-yl)-caproic acid.

Analysis: Calculated for $C_{20}H_{20}O_4$: 74.05%C; 6.22%H. Found: 73.85%C; 6.29%H.

EXAMPLE 31

A mixture of 2.5 g of 4-(6,11-dihydro-11-oxodibenz[b,e]-oxepin-2-yl)butyric acid, Example 28 and 0.2 g of AMBERLITE IR-120H C.P. in 10 ml of isopropyl alcohol is refluxed for 17 hours, cooled, filtered and the solvent removed in vacuo leaving an oil. The oil is dissolved in ether and the ethereal solution is washed successively with water, a 5% aqueous sodium hydroxide solution and water and dried and the ether removed leaving a yellow solid. The solid is recrystallized from hexane to give light yellow crystals, m.p. 47°-49° C, of isopropyl 4-(6,11-dihydro-11-oxodibenz[b,e]-oxepin-2-yl)butyrate.

Analysis: Calculated for $C_{21}H_{22}O_4$: 74.53%C; 6.55%H. Found: 74.38%C; 6.68%H.

EXAMPLE 32

To 10 ml of thionyl chloride is added 5.1 g of 3-(2-carboxybenzyloxy)phenyl acetic acid and the mixture is slowly heated to reflux and allowed to remain at reflux for 2 hours. The excess thionyl chloride is removed under reduced pressure at 90° C to provide diacid chloride. The diacid chloride is dissolved in 25 ml of 1,2-dichloroethane, cooled to between 10° and 15° C and to the cooled solution is added 0.2 g of aluminum chloride. The reaction mixture is stirred at between 10° and 15° C for 4 hours and then poured onto 25 g of ice. The resulting mixture is stirred causing the biphasic mixture to separate. The organic phase is collected and concentrated under reduced pressure, to provide the mono acid chloride. The acid chloride is poured into water and heated to 60° C which hydrolyzes the acid chloride to the free acid. The acid is neutralized with caustic and the solution clarified by treatment with 0.15 g of charcoal and 0.15 g of celite. Re-acidification of the clear solution with 12N hydrochloric acid causes a solid to form which is collected by filtration, washed with water and dried under reduced pressure to provide an off-white crystalline product. Nuclear magnetic resonance spectra and thin layer chromatography confirms the presence of 6,11-dihydro-11-oxodibenz[b,e]oxepin-3-acetic acid.

We claim:

1. A method of treating dermal inflammation which comprises topically administering to the inflamed area of a patient an effective amount of a compound of the formula

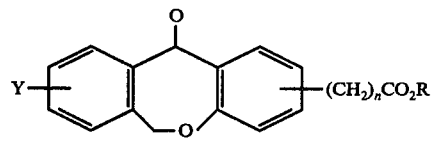

wherein Y is hydrogen, alkyl of from 1 to 4 carbon atoms, alkoxy of from 1 to 4 carbon atoms, halogen or trifluoromethyl; R is hydrogen or straight or branched chain alkyl of from 1 to 6 carbon atoms; and n is an integer of from 1 to 7, or a physiologically tolerable salt thereof.

2. The method of claim 1 in which Y is hydrogen, methyl, methoxy, chloro, bromo, fluoro or trifluoromethyl.

3. The method of claim 2 in which Y is hydrogen.

4. The method of claim 1 in which a compound of the formula

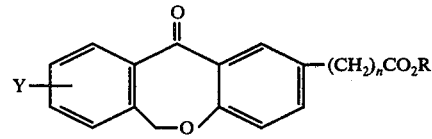

is administered.

5. The method of claim 4 in which Y is hydrogen, methyl, methoxy, chloro, bromo, fluoro or trifluoromethyl.

6. The method of claim 5 in which Y is hydrogen.

7. The method of claim 1 in which 6,11-dihydro-11-oxodibenz[b,e]oxepin-2-acetic acid is administered.

8. The method of claim 1 in which n-butyl 6,11-dihydro-11-oxodibenz[b,e]oxepin-2-acetate is administered.

9. The method of claim 1 in which n-amyl 6,11-dihydro-11-oxodibenz[b,e]oxepin-2-acetate is administered.

10. The method of claim 1 in which methyl 6,11-dihydro-11-oxodibenz[b,e]oxepin-2-acetate is administered.

11. The method of claim 1 in which isopropyl 6,11-dihydro-11-oxodibenz[b,e]oxepin-2-acetate is administered.

12. The method of claim 1 in which 6,11-dihydro-8-chloro-11-oxodibenz[b,e]oxepin-2-acetic acid is administered.

13. The method of claim 1 in which 6,11-dihydro-7-chloro-11-oxodibenz[b,e]oxepin-2-acetic acid is administered.

14. The method of claim 1 in which 6,11-dihydro-9-trifluoromethyl-11-oxodibenz[b,e]oxepin-2-acid is administered.

15. The method of claim 1 in which 6,11-dihydro-8-methoxy-11-oxodibenz[b,e]oxepin-2-acetic acid is administered.

16. The method of claim 1 in which 3-(6,11-dihydro-11-oxodibenz[b,e]oxepin-2-yl)propionic acid is administered.

17. The method of claim 1 in which 4-(6,11-dihydro-11-oxo-dibenz[b,e]oxepin-2-yl)butyric acid is administered.

18. The method of claim 1 in which 8-(6,11-dihydro-11-oxo-dibenz[b,e]oxepin-2-yl)caprylic acid is administered.

19. The method of claim 1 in which 6-(6,11-dihydro-11-oxo-dibenz[b,e]oxepin-2-yl)caproic acid is administered.

20. The method of claim 1 in which methyl 4-(6,11-dihydro-11-oxodibenz[b,e]oxepin-2-yl)butyrate is administered.

21. The method of claim 1 in which isopropyl 4-(6,11-dihydro-11-oxodibenz[b,e]oxepin-2-butyrate is administered.

22. The method of claim 1 in which 6,11-dihydro-11-oxodibenz-[b,e]oxepin-3-acetic acid is administered.

23. The method of claim 1 in which ethyl 6,11-dihydro-11-oxodibenz[b,e]oxepin-2-acetate is administered.

* * * * *